US00PP18870P2

(12) United States Plant Patent
Carruth

(10) Patent No.: US PP18,870 P2
(45) Date of Patent: Jun. 3, 2008

(54) FLORIBUNDA ROSE PLANT NAMED 'WEKCOCBEB'

(50) Latin Name: *Rosa hybrida*
Varietal Denomination: WEKcocbeb

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 47 days.

(21) Appl. No.: 11/603,302

(22) Filed: Nov. 21, 2006

(51) Int. Cl.
*A01H 5/00* (2006.01)

(52) U.S. Cl. ..... Plt./142

(58) Field of Classification Search ..... Plt./142
See application file for complete search history.

*Primary Examiner*—Annette H Para
(74) *Attorney, Agent, or Firm*—McKee, Voorhees & Sease, P.L.C.

(57) ABSTRACT

A new variety of Floribunda rose suitable for garden decoration, having flowers of brilliant scarlet coloration with a white reverse.

1 Drawing Sheet

Classification: The present invention relates to a new *Rosa hybrida* plant.

Variety denomination: The new plant has the varietal denomination 'WEKcocbeb'.

BACKGROUND OF THE INVENTION

This invention relates to a new and distinct variety of Floribunda Rose. It has as its seed parent the variety known as 'POUldron' (U.S. Plant Pat. No. 10,923) and as its pollen parent the variety known as 'WEKplapic' (U.S. Plant Pat. No. 11,517).

SUMMARY OF THE INVENTION

Among the features which distinguish the new variety from other presently available and commercial rose cultivars known to the inventor are the following combination of characteristics: its unusual open bloom form, its red suffusion on the anthers and styles, its dark red new foliage and its brilliant scarlet coloration with a white reverse. The plant has a bushy moderately spreading mature growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKcocbeb' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, 'POUldron' by the following combination of characteristics: whereas 'WEKcocbeb' bears semi-double flowers (about 10 to 17 petals) of brilliant scarlet coloration with a white reverse, 'POUldron' bears very double flowers with significantly heavier petalage (about 44 to 58 petals) of coral pink coloration. The new variety bears many stamens (average about 130), whereas the seed parent bears significantly lesser stamens (average about 80).

The new variety may be distinguished from its pollen parent, 'WEKplapic' by the following combination of characteristics: whereas 'WEKcocbeb' bears semi-double flowers (about 10 to 17 petals) of brilliant scarlet coloration with a white reverse, 'WEKplapic' bears semi-double flowers with significantly lesser petalage (about 9 to 12 petals) of ivory edged red coloration. The new variety has a moderately spreading medium height mature growing habit (about 80 to about 100 cm in height), whereas the pollen parent has a more upright significantly taller mature growing habit (about 90 to about 140 cm. in height).

COMPARISON WITH THE CLOSEST COMMERCIALLY AVAILABLE CULTIVAR

The new variety may be distinguished from its closest commercially available cultivar, 'WEKsacsoul' by the following combination of characteristics: whereas 'WEKcocbeb' bears medium sized flowers (about 7.3 to about 9.4 cm. in diameter) of brilliant scarlet coloration with a white reverse, 'WEKsacsoul' bears significantly smaller flowers (about 5.2 to about 7.9 cm. in diameter) of cerise coloration with yellow center. The new cultivar bears semi-double flowers (about 10 to 17 petals), whereas the closest commercially available cultivar bears single flowers with significantly lesser petalage (about 5 to 6 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966), except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

Botanical designation:

The new variety botanical designation is *Rosa hybrida* 'WEKcocbeb'.

Flower:

The new variety sometimes bears its flowers singly, usually in clusters of two to five or more per stem. Flowers may be borne in regular rounded clusters on strong short to medium length stems (about 16 to about 45 cm.). Outdoors, the plant blooms abundantly and nearly continuously during the growing season. The flowers have a slight apple-like to tea fragrance.

Bud:

The peduncle is about 3.2 to about 5.2 cm. in length, of average caliper (about 0.2 to about 0.3 cm in diameter), and usually erect. It is moderately smooth with some stipitate glands. Peduncle color is between 144A and 146B often moderately suffused, especially on the side exposed to the sun, with between 187B and 183B.

Before the calyx breaks, the bud is about 0.7 to about 1.4 cm. in diameter at the widest point, about 1.5 to about 2.4 cm. in length and very pointed in shape. The surface of the bud bears few foliaceous appendages and many stipitate glands, usually with slender entire foliaceous parts extending beyond the tip of the bud about ½ or more of its length. Bud color is between 144A and 146B sometimes lightly suffused, especially on the side exposed to the sun, with between 187B and 183B.

The sepals are about 2.4 to about 4.2 cm. in length and about 0.6 to about 0.9 cm. in width at the widest point. The outer surface color of the sepal is between 144A and 146B sometimes lightly suffused, especially on the side exposed to the sun, with between 187B and 183B. The inner surface color of the sepal is between 137A and 138B. After the sepals open, the inner surface color in sometimes moderately suffused, especially on the area exposed to the sun, with between 187A and 187B. The inner surface is covered with fine wooly tomentum; sepal margins are lined with few stipitate glands and many hairs.

The receptacle of the flower is of somewhat long length (about 0.5 to about 0.9 cm.) and average in caliper (about 0.5 to about 0.8 cm. in diameter). The receptacle is moderately globular in form. Its surface is very smooth with thick fleshy walls. The receptacle color is between 144A and 146B.

As the petals open (after the calyx breaks), the bud is about 1.3 to about 1.9 cm. in diameter at the widest point, about 1.9 to about 2.8 cm. in length, and moderately ovoid to somewhat pointed in form. The color of the under surfaces of the newly opened petals is between 35C and 23D sometimes heavily suffused with between 53A and 60A sometimes to as dark as 187A. At the point where the petal attaches, there is a very large zone of between 1C and 11B. The color of the upper surfaces of the newly opened petals is between 46B and 45B. At the point where the petal attaches, there is a very large zone of between 2C and 3C.

Bloom:

When fully open, the bloom ranges from about 7.3 to about 9.4 cm. in diameter. Petalage is semi-double with about 10 to 17 petals and about 2 to 8 petaloids irregularly arranged. When partially open, the bloom form is cupped to somewhat globular, and the petals are loosely spiraled to cupped with petal edges moderately reflexed outward. When fully open, the bloom form is more cupped, and the petals are loosely cupped to sometimes somewhat folded laterally with petal edges usually moderately reflexed outward and sometimes somewhat rolled inward.

Petals:

The substance of the petals is somewhat heavy and of moderately thin thickness, with upper surfaces moderately satiny to somewhat velvety and under surfaces slightly shiny to almost matte. The petals are about 3.8 to about 5.7 cm. in length and about 3.4 to about 4.8 cm. in width at the widest point. Petal margins are entire.

The outer and inner petals are broadly obovate in shape with rounded apices.

Petaloids are about 2.4 to about 4.1 cm. in length and about 1.5 to about 3.4 cm. in width at the widest point. Petaloids are irregularly shaped somewhat obovate to oblanceolate with rounded apices.

Newly opened flower:

On the under surfaces of the outer, intermediate and inner petals, the color at the base of the petals is between 9C and 7C, gradually suffusing toward the edge of the petals with between 35D and 12C sometimes moderately suffused, especially on the outermost petals, with between 53A and 60A. The upper surface color of the outer, intermediate and inner petals is between 45A and 46C. At the point where the petal attaches, there is a very large zone of between 9B and 7C.

The upper and upper surface color of the petaloids are similar in coloration to the upper and under surfaces of the outer, intermediate and inner petals.

The general tonality of the newly opened flower is between 45A and 46C with a vary large zone of between 9B and 7C at the base of the flower.

Three-day-old flower:

On the under surfaces of the outer, intermediate and inner petals, the color at the base of the petals is between 155A and 155D, gradually suffusing toward the edge of the petals with between 56D and 55D sometimes moderately suffused, especially on the outermost petals, with between 60B and 60D. The upper surface color of the outer, intermediate and inner petals is between 45A and 51A. At the point where the petal attaches, there is a very large zone of between 155A and 155D.

The under and upper surface color of the petaloids are similar in coloration to the upper and under surfaces of the outer, intermediate and inner petals.

The general tonality of the three-day-old flower is between 45A and 51A with a very large zone of between 155A and 155C at the base of the flower.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

Male reproductive organs:

Stamens are many in number (average about 130) and are arranged regularly about the pistils; a few are mixed with petaloids. The filaments are of irregular length (about 0.4 to about 1.4 cm.) most with anthers. Filaments are between 13B and 12A in color. The anthers are of medium size for the class and all open approximately at the same time. Anther color when immature is near 12A on the external part and near 11C on the internal part usually moderately suffused with near 53A. Anther color at maturity is near 161B on the external part and near 200B on the internal part. Pollen is abundant and between 16B and 17D in color.

Female reproductive organs:

Pistils vary in number (average about 50). The styles are moderately even, somewhat long in length (about 0.4 to about 0.9 cm.), average to moderately heavy in caliper and loosely bunched. Stigma color is near 8D. Style color is between 154D and 154C usually heavily suffused with between 53A and 53B. Ovaries are all enclosed in the calyx.

Hips are moderately long in length (about 1.4 to about 2.1 cm.), rounded to moderately globular in form, and between 30C and 32A in color when ripe. The hip surface is smooth with thick fleshy walls. The sepals are moderately permanent and usually straight in shape.

The seeds are irregularly rounded, smooth in texture, approximately 4 to about 9 per hip, about 0.4 to about 0.6 cm. in diameter at the widest point and between 164C and 161A in color.

Foliage:

The compound leaves are usually comprised of three to seven leaflets and are borne abundantly. The seven-leaflet leaves are about 8.5 to about 14.2 cm. in length and about 5.3 to about 10.6 cm. in width at the widest point, moderately crisp to somewhat leathery in texture and glossy in finish. The terminal leaflets are about 4.8 to about 6.2 cm. in length and about 2.0 to about 3.7 cm. in width at the widest point, shaped oval with acute apices and rounded to somewhat acute bases. Their margins are usually simply serrate.

The upper surface color of the mature leaf is between 147A and 146A. The under surface color of the mature leaf is between 147B and 138B. The upper surface color of the young leaf is between 147B and 137B, usually heavily suffused with between 187A and 183A. The under surface color of the young leaf is between 147B and 138B, usually heavily suffused with between 187B and 183A.

The rachis is average to somewhat heavy in caliper and moderately rough. The upper side is deeply grooved with few hairs and stipitate glands on the edges of the grooves. The under side of the rachis is moderately rough with few hairs and small prickles and some stipitate glands. The rachis color is near 146D on the under side and near 137C on the upper side, often moderately suffused especially on the young leaf with between 187B and 183A.

The stipules are about 1.1 to about 1.7 cm. in length and moderately wide (about 0.5 to about 1.0 cm.) with medium length straight points that usually turn out at an angle of more than 45 degrees and sometimes recurve toward the stem. The stipules color is between 137A and 146B often moderately suffused especially on the young leaf with between 187B and 183A.

The petiole is average to somewhat heavy in caliper and moderately rough. The upper side is deeply grooved with few hairs and stipitate glands on the edges of the grooves. The under side of the petiole is moderately rough with few hairs and small prickles and some stipitate glands. The petiole is about 0.5 to about 1.0 cm. in length and about 0.1 to about 0.2 cm in diameter at the widest point. The petiole color is near 146D on the under side and near 137C on the upper side, often moderately suffused especially on the young leaf with between 187B and 183A.

The plant displays an above average degree of resistance to powdery mildew and rust as compared to other commercial varieties grown under comparable conditions in Upland, Calif. The plant's winder hardiness and drought/heat tolerance are yet to be determined.

Growth:

The plant has a bushy moderately spreading medium height mature growing habit (about 80 to about 100 cm. in height and about 65 to about 80 cm. spread at the widest point), with very full branching. It displays moderately vigorous growth and the canes are of somewhat light caliper for the class.

The color of the major stems is between 146B and 147B. They bear many large prickles that are about 0.06 to about 1.0 cm. in length. The large prickles are almost straight and angled slightly downward with a moderately short narrow oval base; prickle color is between 166B and 166C. The major stem bears many small prickles of similar shape and coloration.

The color of the branches is between 146B and 146A. They bear many large prickles which are of similar size and shape to the large prickles on the major stems; prickle color is between 160A and 162B sometimes lightly suffused with near 187D. The branches bear many small prickles of similar shape and coloration.

The color of the new shoots is between 146C and 146B often moderately suffused with between 187B and 183A. They bear many large prickles which are of similar size and shape to the large prickles on the major stems; prickle color is near 151A usually moderately suffused with between 187B and 187C. The shoots bear many small prickles of similar shape and coloration.

I claim:

1. A new and distinct Floribunda rose plant of the variety substantially as described and illustrated herein.

* * * * *

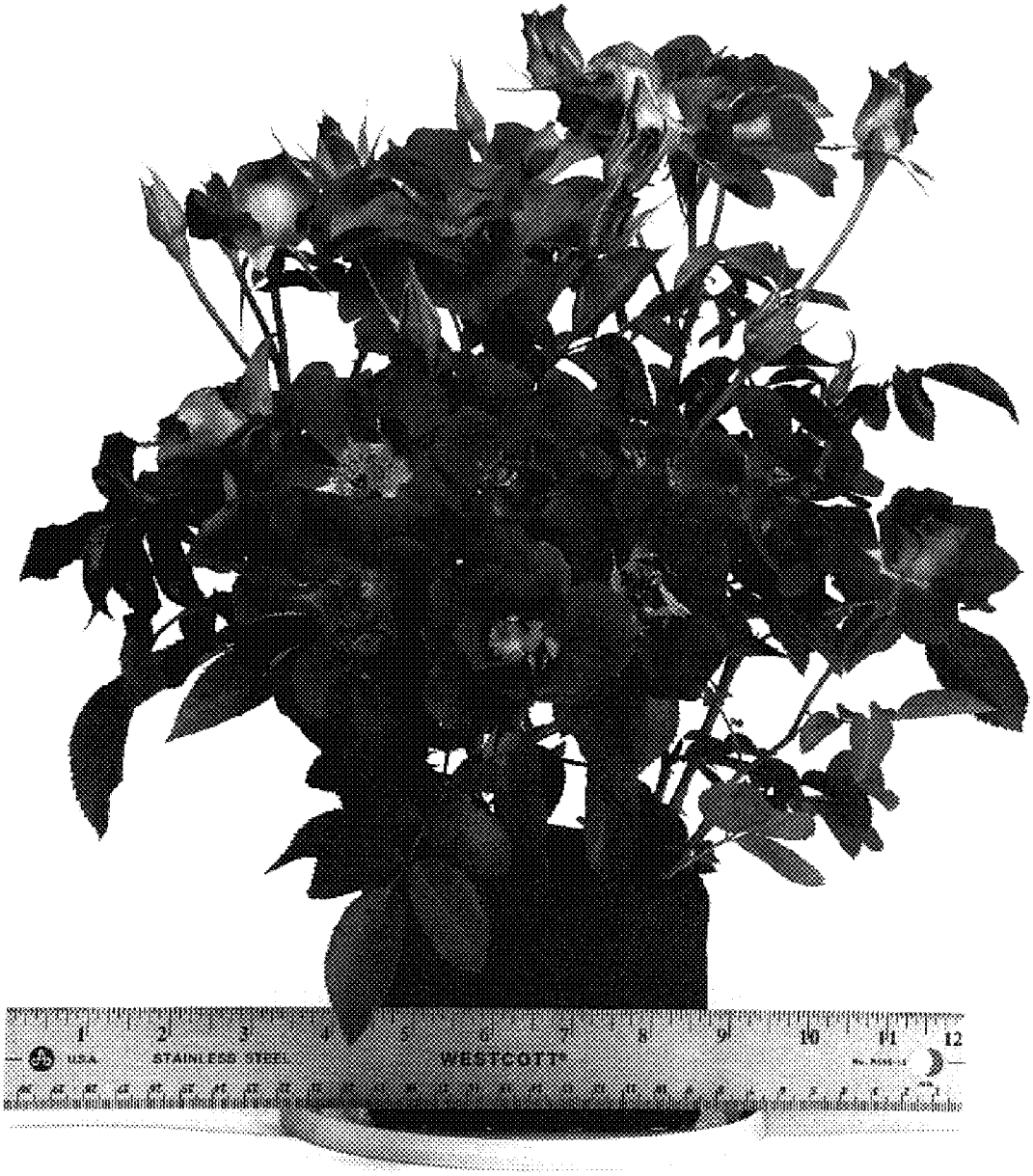
STAINLESS STEEL
WESTCOTT